(12) United States Patent
Daniel

(10) Patent No.: US 9,724,502 B2
(45) Date of Patent: Aug. 8, 2017

(54) DILATOR AND METHOD FOR PENILE PROSTHETIC IMPLANTATION

(71) Applicant: Coloplast A/S, Humlebaek (DK)

(72) Inventor: Geoffrey A. Daniel, Crystal, MN (US)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 14/795,928

(22) Filed: Jul. 10, 2015

(65) Prior Publication Data

US 2017/0007809 A1 Jan. 12, 2017

(51) Int. Cl.
*A61B 17/32* (2006.01)
*A61M 29/00* (2006.01)

(52) U.S. Cl.
CPC .................................. *A61M 29/00* (2013.01)

(58) Field of Classification Search
CPC .......... A61M 29/00; A61M 25/10; A61F 2/26
USPC .......................... 606/159, 170, 198, 190, 191
See application file for complete search history.

(56) References Cited

U.S. PATENT DOCUMENTS

| | | | |
|---|---|---|---|
| 3,196,876 A | 7/1965 | Miller | |
| 3,472,231 A * | 10/1969 | Niebel | A61B 17/1114 606/142 |
| 3,938,529 A * | 2/1976 | Gibbons | A61F 2/04 604/524 |
| 4,154,242 A * | 5/1979 | Termanini | A61M 25/04 604/105 |
| 4,244,370 A | 1/1981 | Furlow et al. | |
| 4,350,151 A | 9/1982 | Brantley | |
| 4,396,021 A | 8/1983 | Baumgartner | |
| 4,585,000 A * | 4/1986 | Hershenson | A61M 29/02 604/108 |
| 4,622,958 A | 11/1986 | Finney | |
| 4,627,838 A * | 12/1986 | Cross | A61M 25/04 604/105 |
| 4,705,041 A | 11/1987 | Kim | |
| 4,932,417 A * | 6/1990 | Ott | A61B 17/00234 600/562 |
| 4,944,226 A * | 7/1990 | Wedertz | F42B 12/105 102/293 |
| 5,074,493 A * | 12/1991 | Greenhalgch | F42B 15/105 244/1 TD |
| 5,217,481 A | 6/1993 | Barbara | |
| 5,342,384 A | 8/1994 | Sugarbaker | |

(Continued)

FOREIGN PATENT DOCUMENTS

DE 9208992 U1 9/1992
DE 60025379 D1 3/2006

(Continued)

*Primary Examiner* — Amy R Weisberg
(74) *Attorney, Agent, or Firm* — Coloplast Corp. Coloplast A/S; Nick Baumann

(57) ABSTRACT

A dilator configured for dilating tissue of a corpora cavernosum of a penis having a dilation body defined along a longitudinal axis of the dilator and an extendable wing connected to the dilation body. A knob is provided at a first proximal end portion of the dilation body and is configured to communicate with the extendable wing. Rotating the knob extends the extendable wing away from the dilation body and changes an effective diameter of the dilator. Also disclosed is a method of dilating the corpora cavernosum of a penis and a method of implanting a penile prosthetic in the corpora cavernosum of a penis.

14 Claims, 9 Drawing Sheets

(56) References Cited

U.S. PATENT DOCUMENTS

| | | | | |
|---|---|---|---|---|
| 5,409,460 | A * | 4/1995 | Krumme | A61M 29/02 604/107 |
| 5,458,612 | A | 10/1995 | Chin | |
| 5,588,965 | A | 12/1996 | Burton et al. | |
| 5,695,515 | A * | 12/1997 | Orejola | A61M 29/02 606/191 |
| 5,868,729 | A | 2/1999 | Pelfrey | |
| 5,935,107 | A * | 8/1999 | Taylor | A61J 15/0015 604/164.04 |
| 5,968,067 | A * | 10/1999 | Mooreville | A61F 2/26 600/40 |
| 6,102,929 | A | 8/2000 | Conway et al. | |
| 6,565,583 | B1 * | 5/2003 | Deaton | A61B 17/22 606/127 |
| 6,589,214 | B2 * | 7/2003 | McGuckin, Jr. | A61M 25/0662 604/165.03 |
| 6,808,489 | B2 | 10/2004 | George et al. | |
| 6,916,330 | B2 | 7/2005 | Simonson | |
| 7,261,688 | B2 * | 8/2007 | Smith | A61B 17/0293 600/190 |
| 7,354,017 | B2 * | 4/2008 | Morris | F42B 10/54 102/501 |
| 7,651,529 | B2 * | 1/2010 | Gellman | A61F 2/04 606/198 |
| 7,922,647 | B2 | 4/2011 | Slattery et al. | |
| 7,938,842 | B1 | 5/2011 | Chin | |
| 9,086,258 | B1 * | 7/2015 | Vasudevan | F42B 15/01 |
| 2002/0055756 | A1 | 5/2002 | Thornton | |
| 2002/0198558 | A1 | 12/2002 | Briscoe et al. | |
| 2004/0087994 | A1 * | 5/2004 | Suddaby | A61B 17/8858 606/190 |
| 2004/0097997 | A1 | 5/2004 | Di Cecco | |
| 2004/0193190 | A1 * | 9/2004 | Liddicoat | A61B 17/00234 606/153 |
| 2004/0220522 | A1 | 11/2004 | Briscoe et al. | |
| 2005/0004504 | A1 * | 1/2005 | Frye | A61M 1/3661 604/6.16 |
| 2005/0004593 | A1 | 1/2005 | Simonson | |
| 2005/0075534 | A1 | 4/2005 | Kuyava | |
| 2005/0119695 | A1 * | 6/2005 | Carley | A61B 17/0057 606/213 |
| 2005/0203559 | A1 * | 9/2005 | O'Heeron | A61B 17/3417 606/185 |
| 2006/0071120 | A1 * | 4/2006 | Selin | F42B 10/64 244/3.27 |
| 2006/0229553 | A1 * | 10/2006 | Hammack | A61M 25/04 604/96.01 |
| 2006/0235458 | A1 * | 10/2006 | Belson | A61M 25/0032 606/191 |
| 2007/0005093 | A1 * | 1/2007 | Cox | A61B 17/320016 606/198 |
| 2007/0241227 | A1 * | 10/2007 | Zemany | F41G 7/222 244/3.1 |
| 2007/0282352 | A1 * | 12/2007 | Carley | A61B 17/0057 606/142 |
| 2008/0114367 | A1 * | 5/2008 | Meyer | A61B 17/025 606/90 |
| 2008/0183204 | A1 * | 7/2008 | Greenhalgh | A61B 17/8858 606/198 |
| 2008/0319475 | A1 * | 12/2008 | Clark | A61B 17/0057 606/213 |
| 2009/0082731 | A1 * | 3/2009 | Moreno | A61B 17/3439 604/158 |
| 2009/0090809 | A1 * | 4/2009 | Ronn | F42B 10/14 244/3.28 |
| 2010/0057130 | A1 * | 3/2010 | Yue | A61B 17/7065 606/249 |
| 2010/0160722 | A1 | 6/2010 | Kuyava et al. | |
| 2010/0168790 | A1 * | 7/2010 | Clark | A61B 17/0057 606/213 |
| 2010/0262166 | A1 * | 10/2010 | Boraiah | A61B 17/0057 606/148 |
| 2011/0144427 | A1 | 6/2011 | Morningstar et al. | |
| 2011/0144440 | A1 * | 6/2011 | Cropper | A61B 17/3421 600/203 |
| 2011/0297783 | A1 * | 12/2011 | Martinez | F42B 10/14 244/3.21 |
| 2014/0121583 | A1 * | 5/2014 | Duncan | A61M 25/02 604/8 |
| 2014/0316209 | A1 * | 10/2014 | Overes | A61B 17/0218 600/206 |
| 2015/0217100 | A1 * | 8/2015 | Karino | A61B 1/307 604/22 |
| 2017/0007809 | A1 * | 1/2017 | Daniel | A61M 29/00 |

FOREIGN PATENT DOCUMENTS

| | | |
|---|---|---|
| FR | 2532551 A1 | 3/1984 |
| WO | 95/03848 | 2/1995 |
| WO | 02102230 A2 | 12/2002 |
| WO | 03071970 A1 | 9/2003 |
| WO | 2008/008547 | 1/2008 |
| WO | 2011079847 A1 | 7/2011 |

* cited by examiner

DILATOR AND METHOD FOR PENILE PROSTHETIC IMPLANTATION

SUMMARY

A first aspect provides a dilator configured for dilating tissue of a corpora cavernosum of a penis according to claim 1. The following specification provides further advantageous embodiments of the present disclosure. A second aspect provides a method for dilating a corpora cavernosum of a penis. A third aspect provides a method of implanting a penile prosthetic in a corpora cavernosum of a penis.

BRIEF DESCRIPTION OF THE DRAWINGS

The accompanying drawings are included to provide a further understanding of embodiments and are incorporated in and constitute a part of this specification. The drawings illustrate embodiments and together with the description serve to explain principles of embodiments. Other embodiments and many of the intended advantages of embodiments will be readily appreciated as they become better understood by reference to the following detailed description. The elements of the drawings are not necessarily to scale relative to each other.

DETAILED DESCRIPTION

Figure 1B:
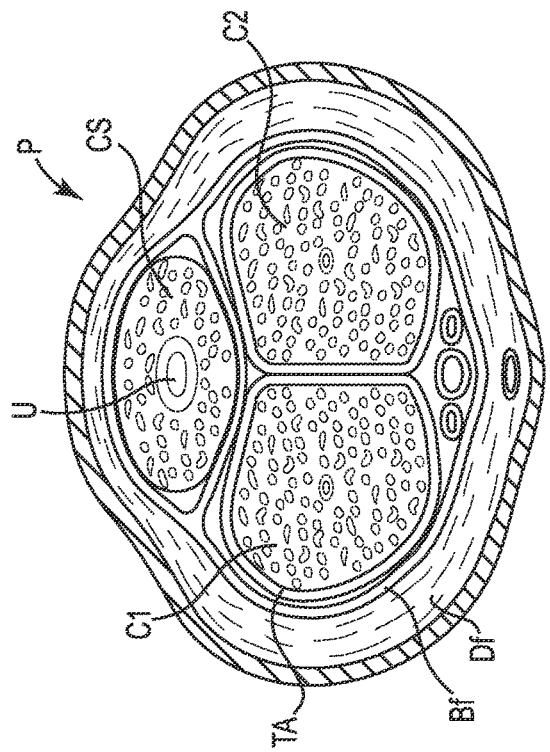
FIG. 1A is a perspective view of a prior art penile prosthetic cylinder attached to suture and a needle for implanting the cylinder into a penis illustrated in FIG. 1B.

In the following Detailed Description, reference is made to the accompanying drawings, which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the attached claims.

The features of the various exemplary embodiments described in this application may be combined with each other, unless specifically noted otherwise.

The term "proximal" in this application means that part that is situated next to or near the point of attachment or origin or a central point; for example, as located toward a center of the human body. The prostate is proximal relative to skin of the patient.

The term "distal" in this application means that part that is situated away from the point of attachment or origin or the central point; for example, as located away from the center of the human body. The glans penis is distal relative to the crus penis of the patient.

End means endmost. A distal end is the furthest endmost location of a distal portion of a thing being described, whereas a proximal end is the nearest endmost location of a proximal portion of the thing being described. The portion next to or adjacent to an end is an end portion. For example, a 12 inch ruler has a center point at 6 inches, a first end at zero inches and a second, opposite end at 12 inches, an end portion adjacent to the first end and another end portion adjacent to the second end.

The term "effective diameter" in this application means the greatest diameter of a surgical tool in a given state of that tool. For example, if the tool is provided with a wing deployed in a given state and subsequently rotated one full revolution about its longitudinal axis, the effective diameter will correspond to a diameter of the circle scribed by the wing in that given state as a result of that rotation.

A penile prosthetic typically includes two cylinders implanted in the penis, a pump implanted in the scrotum or other internal space, and a liquid holding reservoir implanted in the abdomen or other internal space. The surgeon usually implants the reservoir last, after confirming that the tubing attached to the reservoir, pump, and cylinders is not leaking. The reservoir is filled with saline or another liquid at approximately atmospheric pressure. The pump is employed to transfer the liquid from the reservoir to the cylinders, and in so doing, the liquid in the cylinders is pressurized to create an erection. A flow path is provided to depressurize and return the liquid from the cylinders back to the reservoir.

Figure 1A:
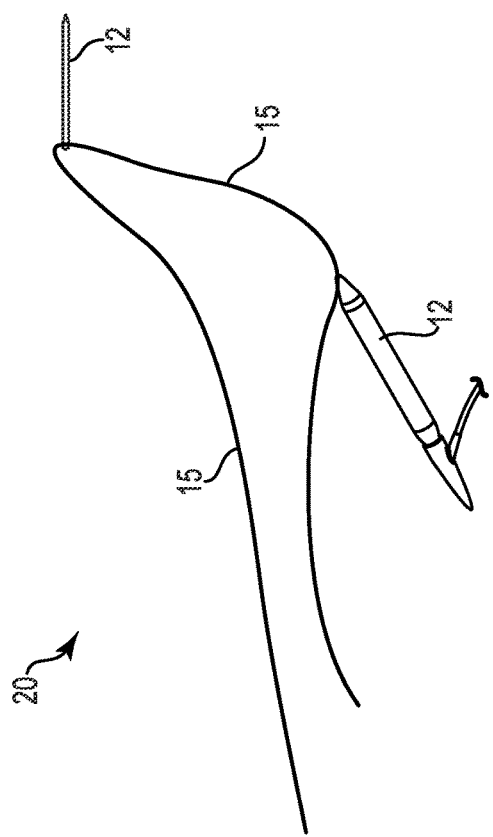

In some approaches, an inflatable cylinder 12 as shown by way of example in FIG. 1A is to be implanted into a penis P illustrated in FIG. 1B. FIG. 1B is a cross-sectional view of the penis P oriented to access by the surgeon. The surgeon gains access to the corpora cavernosa though small incisions, and with this in mind, the cross-sectional view of FIG. 1B is not the view observed by the surgeon. In the view of FIG. 1B the penis P of the patient is reclined against the torso such that the urethra U, surrounded by corpus spongiosum tissue, is oriented upward.

In preparation for the implantation of the penile prosthesis, the groin area of the patient is shaved, cleaned and suitably prepped with a surgical solution prior to draping with a sterile drape as directed by the healthcare provider's procedures. A retraction device, such as a retractor sold under the trademark Lone Star and available from Lone Star Medical Products of Stafford, Tex., is placed around the penis P. A catheter is inserted into the urethra U from the distal end of the penis P into the bladder. Thereafter, the surgeon forms an incision to access the corpora cavernosa C1 and C2 of the penis.

Suitable examples of incisions include either an infrapubic incision or a transverse scrotal incision. The infrapubic incision is initiated between the umbilicus and the penis (i.e., above the penis), whereas the transverse scrotal incision is made across an upper portion of the patient's scrotum.

In the transverse scrotal approach the surgeon forms a 2-3 cm transverse incision through the subcutaneous tissue of the median raphe of the upper scrotum and dissects down through the Darto's fascia Df and Buck's fascia Bf to expose the tunicae albuginea TA of the penis P. Thereafter, each corpora cavernosum C1 and C2 is exposed in a corporotomy where a small (approximately 1.5 cm) incision is formed to allow the surgeon to access to the corpora cavernosa C1 and C2.

Each corpora cavernosum C1, C2 is dilated to form a recess in the penis P that is sized to receive a cylinder 12. In some approaches, the step of dilating the corpora cavernosum involves using a number of progressively larger sized dilation tools in turn being inserted into the corpora cavernosum. The surgeon may choose to begin the dilation procedure with a dilation tool of a smallest available diameter, e.g. using a first tool of 8 mm diameter, then moving on to a 10 mm tool, a 12 mm tool and so forth depending on patient requirements. Such dilation procedure involves the potential use of a relatively large number of individual tools or fittings that need to be readily available as a full set of dilator tools before each implantation procedure.

After having dilated the cavernosum C1, C2, in one known approach, a suture 15 is inserted through the distal, leading end of the cylinder 12 and through a needle 14. With the aid of a special tool, known in the art as a Furlow tool, the needle 14 is pushed through the glans penis. The surgeon captures the needle 14, disengages the needle 14 from the suture, and pulls on the suture 15 to draw the cylinder 12 into the dilated corpora cavernosum. The suture 15 is disengaged from the cylinder 12, which is now implanted within the corpora cavernosum C1 or C2.

Embodiments provide a dilator for dilating tissue of a corpora cavernosum having an extendable wing that can be adjusted to have a range of different diameters and thereby eliminates the need for a full set of dilator tools.

Embodiments provide a dilator for dilating tissue of a corpora cavernosum that can be used as an alternative to a Furlow tool.

Embodiments provide a dilator for dilating tissue of a corpora cavernosum that can be used as an alternative to a cavernatome.

Embodiments provide a dilator for dilating tissue of a corpora cavernosum that reduces the overall number of necessary tools for dilation of the corpora and implantation of a penile prosthetic.

Embodiments provide a method for dilating tissue of a corpora cavernosum that reduces the overall number of surgical tools involved.

Embodiments provide a method of implanting a penile prosthetic in the corpora cavernosum of a penis that reduces the overall number of surgical tools involved.

Figure 2:
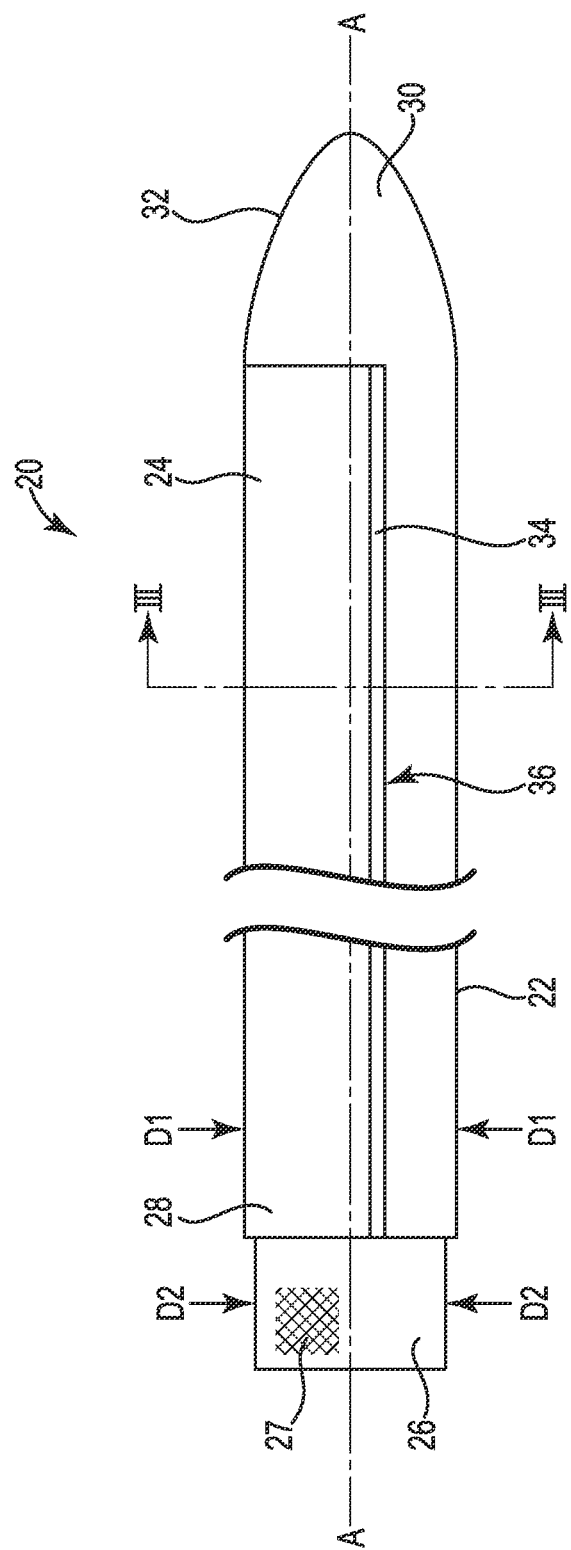
FIG. 2 is a side view of one embodiment of a dilator for dilating tissue of a corpora cavernosum of a penis.

FIG. 2 is a side view of one embodiment of a dilator 20 for dilating tissue of a corpora cavernosum of a penis according to a first aspect of the present disclosure. The dilator 20 includes a dilation body 22 defined along a longitudinal axis A-A of the dilator. The dilator 20 includes an extendable wing 24 connected to the dilation body 22. In one embodiment, a knob 26 is provided at a first proximal end portion 28 of the dilation body 22. In one embodiment, the knob 26 is connected to the extendable wing 24. In one embodiment, the knob 26 is configured to communicate with the extendable wing 24 in such a way that actuation of the knob 26 moves the extendable wing 24 with respect to the dilation body 22 to change an effective diameter (see FIGS. 3A-3B) of the dilator 20.

In one embodiment, the dilation body 22 extends between the first proximal end portion 28 and a second distal end portion 30 of the dilator 20. In one embodiment, the extendable wing 24 is configured to extend from the first proximal end portion 28, along the longitudinal axis A-A of the dilator and along a portion that is less than an entirety of the dilation body 22. In one embodiment, the extendable wing 24 extends along a portion that is between 50-90% of a total longitudinal extent of the dilation body 22. Configuring the extendable wing 24 with a longitudinal extent less than that of the full length of the dilator 20 provides for possible adaptation to different patient anatomies and possible customized controlling of the dilator 20 depending on the particular task at hand. In one embodiment, at 32, the dilation body 22 tapers toward a central longitudinal axis of the dilator 20 at the second distal end portion 30 of the dilation body 22. This is useful in that in some situations, the surgeon prefers not to dilate or remove tissue directly below the penis glans at a distal end of the corpora cavernosum. In one embodiment, the extendable wing 24 includes a tip portion 34 defined at a free edge 36 of the extendable wing 24. The term "free edge" is to be understood as the edge 36 not being attached to any other portion of the dilator 20. The tip portion 34 is to be understood as being an end portion of the extendable wing. The tip portion 34 is integral with the extendable wing 24 and the edge of the tip portion 34 is free and does not connect or engage with other portions or parts of the dilator 20.

In one embodiment, the knob 26 takes a circular outer surface shape. This provides for easy gripping and intuitive handling. In one embodiment, the knob 26 has a knob diameter D2 corresponding to a diameter D1 of the dilator 20 in a first closed state of the dilator 20. This configuration streamlines the outer surface of the dilator. Other suitable shapes of the knob 26 are acceptable. In one embodiment, an outer surface of the knob 26 includes a surface portion providing increased friction for better finger gripping, e.g. a criss-cross pattern or indentations 27.

Figure 3A:
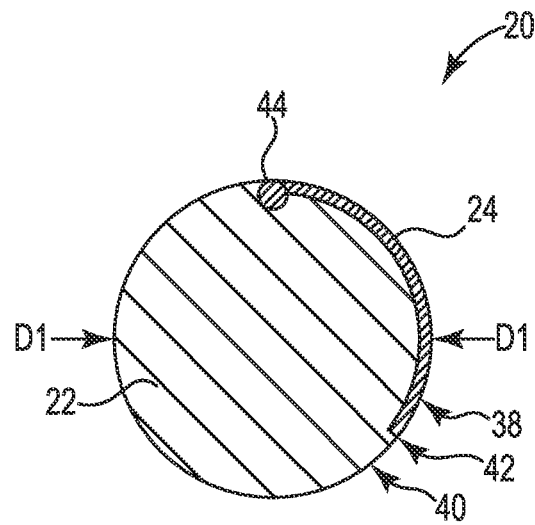
FIGS. 3A and 3B are cross-sectional views of one embodiment of the dilator taken along line III-III in FIG. 2 and showing the dilator in two different situations.
Figure 3B:
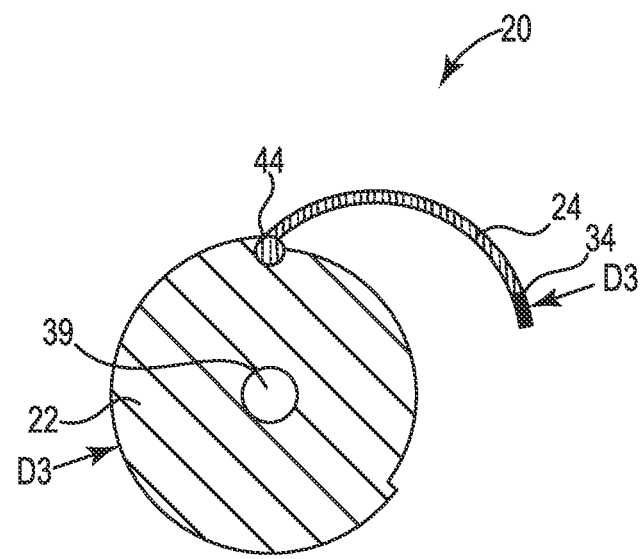

FIG. 3A is a cross-sectional view of one embodiment of the dilator 20 taken along line III-III in FIG. 2 and showing the dilator 20 with the extendable wing 24 not extended and located in contact with the dilation body 22. In one embodiment, the situation shown in FIG. 3A corresponds to a first closed state of the dilator 20. FIG. 3B is another cross-sectional view along line III-III in FIG. 2 showing the dilator 20 with the extendable wing 24 extended away from the dilation body 22. In one embodiment, the situation shown in FIG. 3B corresponds to a second open state of the dilator 20. In one embodiment, in the first closed state of the dilator 20, a first external surface 38 of the extendable wing 24 is configured to be flush with a second external surface 40 of the dilation body 22. In other words, in the closed state of the dilator 20, there are no bumps or unevenness in the outer contour of the dilator 20 at a transition 42 between the first external surface 38 and the second external surface 40. This ensures a smooth outer surface of the dilator, which is useful for at least reasons of secure insertion into and extraction of the dilator 20 from the corpora cavernosum. In the situation shown in the view of FIG. 3A, the dilator 20 has a first effective diameter D1. In the situation shown in the view of FIG. 3B, the extendable wing 24 has been moved with respect to the dilation body 22, thereby providing a larger second effective diameter D3 of the dilator 20. In embodiments, the extendable wing 24 is operable to increase the effective diameter of the dilator 20 up to two times. In embodiments, the extendable wing 24 is operable to increase the effective diameter of the dilator 20 in a range from 10-200%, preferably 50-150%, more preferably 60-100%. This is useful in that the dilator 20 can accommodate a large number of patient anatomies and reduces requirement for having a plurality of dilator tools with different diameters available. FIGS. 3A and 3B also show a hinge point 44 in which the extendable wing 24 is connected to the dilation body 22. In one embodiment, the extendable wing 24 is configured to pivot around its connection in the hinge point 44. In one embodiment, actuation of the knob 26 in a first direction effects a pivoting of the extendable wing 24 around the hinge point 44. In one embodiment, actuation of the knob 26 in the first direction effects a movement of the extendable wing 24 around the hinge point 44 such that the tip portion 34 is a portion of the extendable wing 24 that moves the furthest away from the dilation body 22. The extendable wing 24 does not move away from the dilation body 22 at its connection at the hinge point 44. In one embodiment, the dilation body 22 is solid, or partly solid, over a portion or all of its longitudinal extent. In one embodiment, the dilation body 22 is partly solid and includes an internal canal 39 extending along a portion or throughout the longitudinal extent of the dilation body 22. In one embodiment, a first opening of the internal canal is provided at the first proximal end 28 of the dilation body 22 and a second opening of the internal canal 39 is provided at the second, distal end 30 of the dilation body 22. In one embodiment, the internal canal 39 and the first and second openings are configured to receive a plunger. The plunger can be loaded with a Keith needle. Thereby, the internal canal 39 and the first and second openings are useful for additionally adapting the dilator to be used instead of and avoid the use of a traditional Furlow tool for the implantation procedure, in turn saving time and resources. In one embodiment, the dilation body 22 is configured to be hollow over a portion or all of its longitudinal extent. Potentially advantageous effects of providing a fully or partly hollow dilation body 22 are that the dilator can be made lightweight and/or for single-use.

Figure 4:
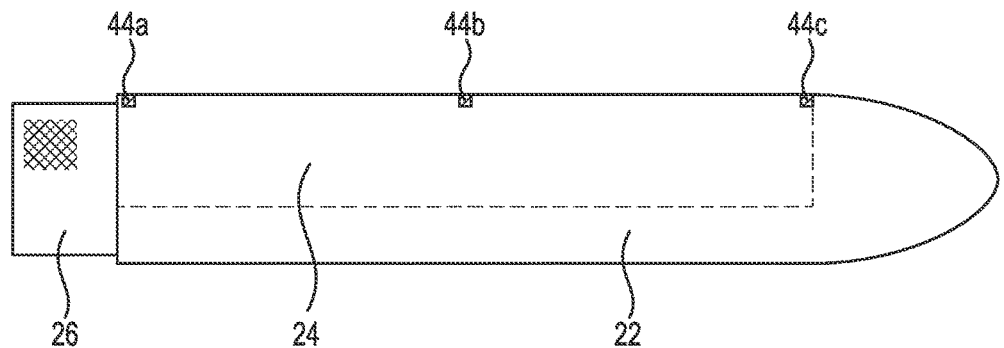
FIG. 4 is a side view showing one embodiment of the dilator including a plurality of individual hinge points for connecting the extendable wing to the dilation body.

FIG. 4 is a side view showing one embodiment of the dilator 20 wherein a plurality of individual hinge points 44a, 44b, 44c are configured along the longitudinal extent of the dilation body 22 for connecting the extendable wing 24 to the dilation body 22. For purposes of better illustrating the hinge points, the extendable wing 24 is indicated with a dotted line in FIG. 4. In embodiments, the extendable wing 24 is connected to the dilation body 22 in two, three or more than three hinge points 44. In one embodiment, the connection between the extendable wing 24 and the hinge point 44 includes a snap-fit coupling. Other types of connections or couplings between the extendable wing 24 and the dilation body 22 are acceptable.

Figure 5:
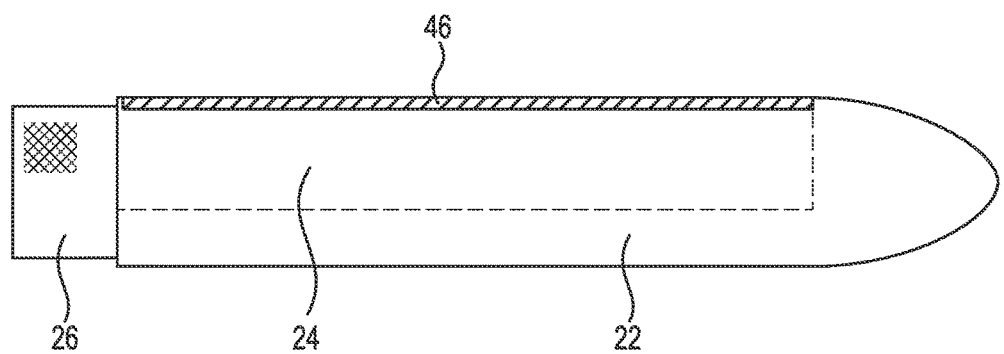
FIG. 5 is a side view showing one embodiment of the dilator including a continuous turn rod for connecting the extendable wing to the dilation body.

FIG. 5 is another side view showing one embodiment of the dilator 20 wherein a continuous turn rod 46 is configured along the longitudinal extent of the dilation body 22 for connecting the extendable wing 24 to the dilation body 22 along the whole extent of the turn rod 46. For purposes of better illustrating the turn rod 46, the extendable wing 24 is shown with a dotted line in FIG. 5. In one embodiment, the extendable wing 24 is welded to the turn rod 46. In one embodiment, the extendable wing 24 is glued, or adhered to the turn rod 46. In one embodiment, the extendable wing 24 and the turn rod 46 are manufactured as a monolithic entity with the turn rod 46 configured to be movably connected to the dilation body 22. In one embodiment, the turn rod 46 is a continuous turn rod, i.e. not provided in sections or segments.

Figure 6:
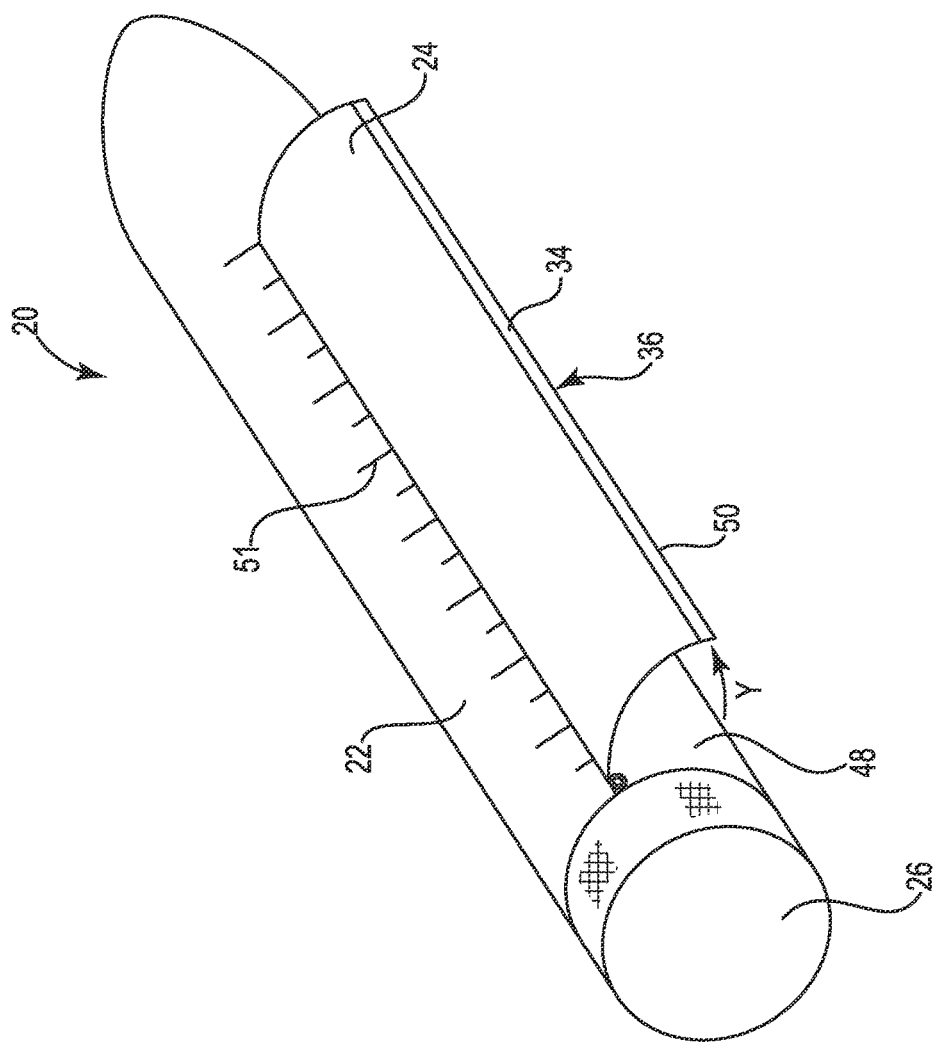
FIG. 6 is a perspective view showing one embodiment of the dilator in a situation wherein the extendable wing is extended away from the dilation body.

FIG. 6 is a perspective view showing one embodiment of the dilator 20 in a situation wherein the extendable wing 24 is extended away from the dilation body 22. The knob 26 is configured to communicate with the extendable wing 24. When the knob 26 is turned in a first direction, the free edge 36 of the extendable wing 24 moves away from a body surface 48 of the dilation body 22 in the direction of arrow Y. Depending on requirements, in embodiments, the extendable wing 24 can be configured to provide the dilator 20 with an effective diameter D3 of up to twice the diameter D1. When the extendable wing 24 is extended from the dilation body 22, the dilator 20 can be rotated, or turned, around the longitudinal axis A-A such that the rotation of the dilator 20 causes dilation of tissue in contact with the extended wing 24. In one embodiment, the tip portion 34 at the free edge 36 includes a blade 50. In one embodiment, the blade 50 is a sharp surgical blade. One advantageous effect of providing the blade 50 is that it helps provide for the dilator 20 to additionally be adapted for use as a cavernatome. Configuring the dilator 20 with the blade 50 further provides for the use of one less individual tool during the implant procedure (i.e. a dedicated cavernatome tool). In one embodiment, the blade 50 is adapted for skiving tissue within the corpora cavernosum when the dilator 20 is rotated. In one embodiment, the dilator 20 includes measurement indicia 51 provided along an external surface of the dilation body 22. The measurement indicia are useful in helping the surgeon determine the right size of cylinder to be implanted.

Figure 7:
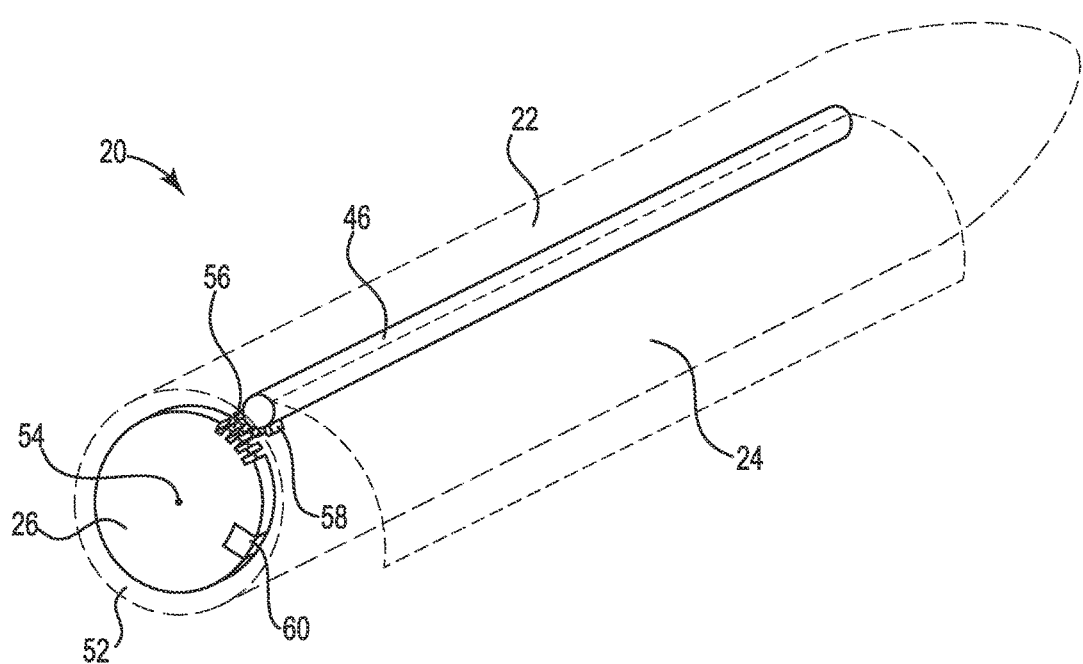
FIG. 7 is a schematic, perspective view of a portion of the dilator according to one embodiment.

FIG. 7 is a schematic, perspective view of a portion of the dilator 20 according to one embodiment. The dilation body 22 and the extendable wing 24 are shown in phantom line, whereas the knob 26 and a turn rod 46 is shown in full lines. In one embodiment, the knob 26 is connected to the dilation body 22 at a proximal end surface 52 of the dilation body. In one embodiment, the knob 26 is connected to the dilation body 22 such that it is rotatable around a central connection rod 54, the central connection rod 54 connected to the knob 26 and to the dilation body 22 at the proximal end surface 52. In one embodiment, a portion of an outer periphery of the knob 26 is adapted as a gear 56 having a plurality of gear teeth configured to communicate with a corresponding gear 58 on a portion of a periphery of the turn rod 46. The turn rod 46 is connected to the extendable wing 24 and is also rotatably connected to the dilation body 22. In embodiments, in a first, closed state of the dilator 20, the extendable wing 24 is flush with the second external surface 40 of the dilation body 22 (see FIG. 3A). In one embodiment as shown in FIG. 7, actuating the knob 26 by rotating it in a clockwise direction causes the extendable wing 24 to extend away from the dilation body 22 as the gears 56 and 58 communicate to transfer the rotation of the knob 26 into a rotation of the turn rod 46. In one embodiment, counterclockwise rotation of the knob 26 causes the extendable wing 24 to move toward the dilation body 22. In one embodiment, counterclockwise rotation of the knob 26 makes the extendable wing 24 return to its initial position in which it is flush with the second external surface 40 of the dilation body 22.

Figures 8A, 9A:
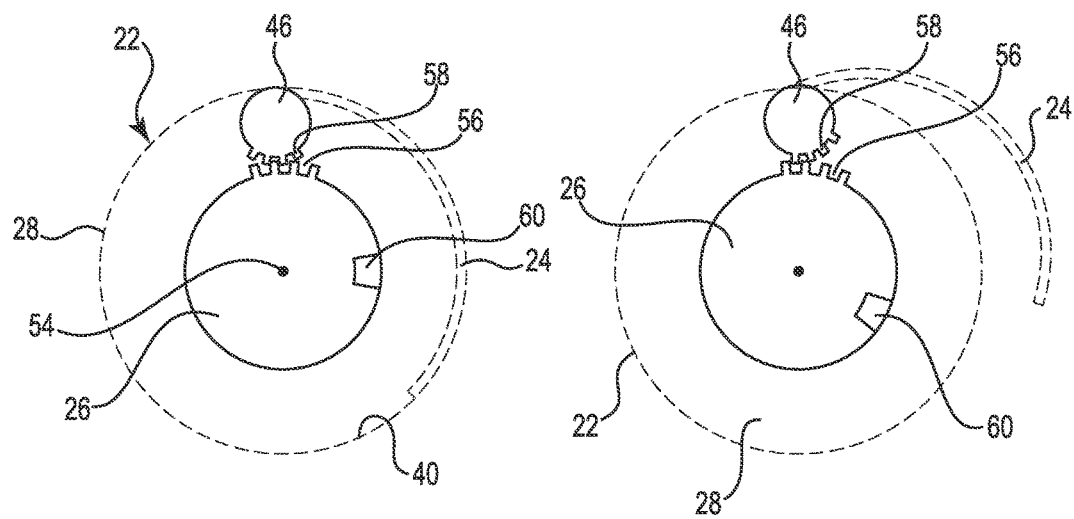
FIG. 8A is an end view of one embodiment of the first proximal end of the dilation body.
FIG. 9A is an end view of one embodiment of the first proximal end of the dilation body wherein the knob is rotated to extend the extendable wing away from the dilation body.

FIG. 8A is an end view of one embodiment of the first proximal end 28 of the dilation body 22. The extendable wing 24 and the dilation body 22 is indicated in phantom line in the view of FIG. 8A. The knob 26 and a proximal end of the turn rod 46 is shown in full line. The gears 56 and 58 are also indicated. FIG. 8A shows a situation in which the extendable wing 24 is not extended from the dilation body 22 and is flush with the second external surface 40 of the dilation body 22. In one embodiment, the dilator 20 includes a locking mechanism that is configured to maintain the extendable wing 24 extended away from the dilation body 22. In one embodiment, the lock includes a lock button 60. In one embodiment, the lock button is provided in a portion of the knob 26.

Figures 8B, 9B:
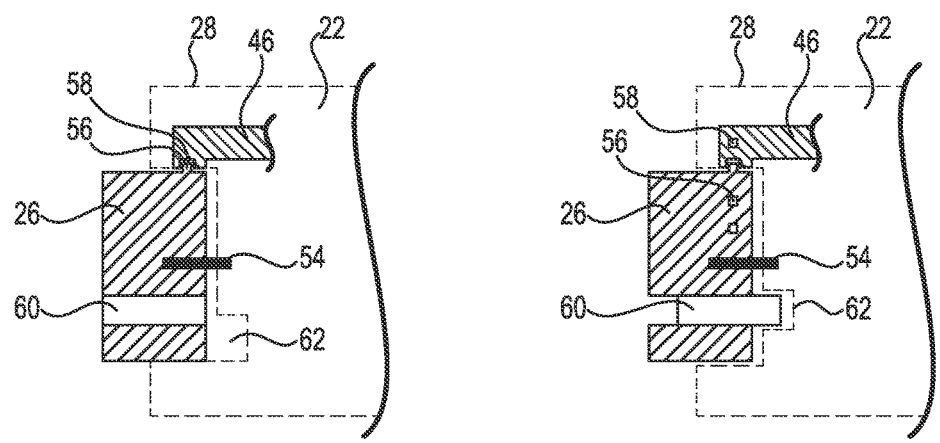
FIG. 8B is a schematic side view showing one embodiment of the first proximal end of the dilation body corresponding to the embodiment shown in the view of FIG. 8A.
FIG. 9B is a schematic side view showing one embodiment of the first proximal end of the dilation body corresponding to the embodiment shown in the view of FIG. 9A.

FIG. 8B is a schematic side view showing one embodiment of the first proximal end 28 of the dilation body 22 and corresponding to the embodiment shown in the view of FIG. 8A. For illustration purposes, in FIG. 8B the gears 56 and 58 are shown adjacent, but not contacting each other. It is to be understood that in use the teeth of the gears 56 and 58 engage with each other. In FIG. 8B, as in FIG. 8A, the extendable wing 24 (not shown) is not extended from the dilation body 22. In one embodiment, the situation in FIGS. 8A and 8B correspond to a first, closed state of the dilator 20. In one embodiment, in the first closed state, the knob 26 has not been actuated or rotated such that the extendable wing 24 is flush with the second external surface 40 of the dilation body 22. The central connection rod 54 is also visible in FIG. 8B. In one embodiment corresponding to the situation shown in FIGS. 8A and 8B the knob 26 is not rotated around a central axis through the central connection rod 54. In this situation, the lock button 60 is not in alignment with lock slot 62 defined in the first proximal end 28 of the dilation body 22.

FIG. 9A is an end view of one embodiment of the first proximal end 28 of the dilation body 22 wherein the knob 26 is rotated to extend the extendable wing 24 away from the dilation body 22 (the wing and the dilation body shown in phantom line). In this situation, the knob 26 is actuated and rotated clockwise to rotate the turn rod 46 counterclockwise via the gears 56 and 58 to extend the extendable wing 24 connected to the turn rod 46 from the dilation body 22. The clockwise rotation of the knob 26 also effects a change of position of the lock button 60 provided in a portion of the knob 26.

FIG. 9B is another schematic side view showing one embodiment of the first proximal end 28 of the dilation body 22 and corresponding to the embodiment shown in the view of FIG. 9A. In the situation shown, the extendable wing 24 (not shown) has been extended from the dilation body 22 and the locking mechanism is engaged by pushing the lock button 60 into the lock slot 62, thereby providing a stop for any further rotation of the knob in either the clockwise or counterclockwise direction. In one embodiment, the locking mechanism is configured to be engageable and disengageable by pressing the lock button 60 in sequence, e.g. using a spring mechanism similar to that of a retractable ballpoint pen. For illustration purposes, distances between the individual parts in FIG. 9A are shown exaggerated. For instance, it is to be understood that the locking mechanism is configured to allow the lock button 60 to enter and exit the lock slot 62 in an axial direction parallel to the longitudinal axis of the dilation body 22, but it does not allow any sideways movement of the lock button 60 when engaged in the lock slot 62. In embodiments, more than one, or alternatively a larger lock slot 62 can be provided in the first proximal end 28 of the dilation body 22. In embodiments, a plurality of lock slots 62 is provided to allow locking of the extendable wing 24 in different positions such that the dilator 20 can be set to a plurality of different effective diameters D3. Other locking mechanisms are acceptable.

Figure 10:
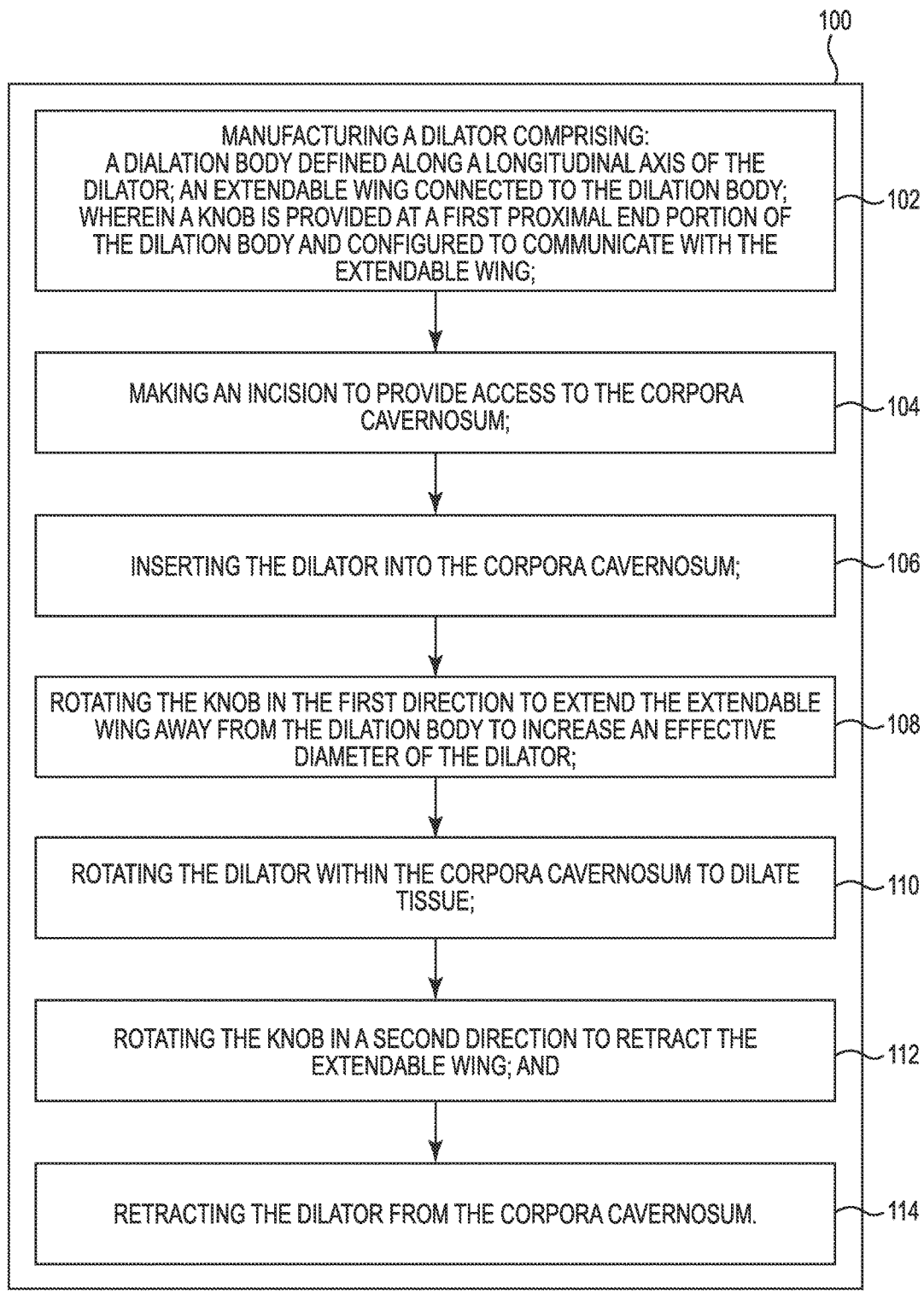
FIG. 10 is a box diagram indicating a method of dilating tissue of a corpora cavernosum of a penis.

In a second aspect, the present disclosure relates to a method 100 of dilating tissue of a corpora cavernosum of a penis. FIG. 10 is a box diagram indicating the method 100. At 102, the method includes manufacturing a dilator comprising: a dilation body defined along a longitudinal axis of the dilator and an extendable wing connected to the dilation body, wherein a knob is provided at a first proximal end portion of the dilation body and configured to communicate with the extendable wing. In embodiments, the dilator is a dilator according to the embodiments of the first aspect of the present disclosure. At 104, the method includes making an incision to provide access to the corpora cavernosum. Suitable examples of incisions are provided above. At 106, the method includes inserting the dilator into the corpora cavernosum. At 108, the method includes rotating the knob in a first direction to extend the extendable wing away from the dilation body to increase an effective diameter of the dilator. At 110, the method includes rotating the dilator within the corpora cavernosum to dilate tissue. At 112, the method includes rotating the knob in a second direction to retract the extendable wing. At 114, the method includes retracting the dilator from the corpora cavernosum.

Figure 11:
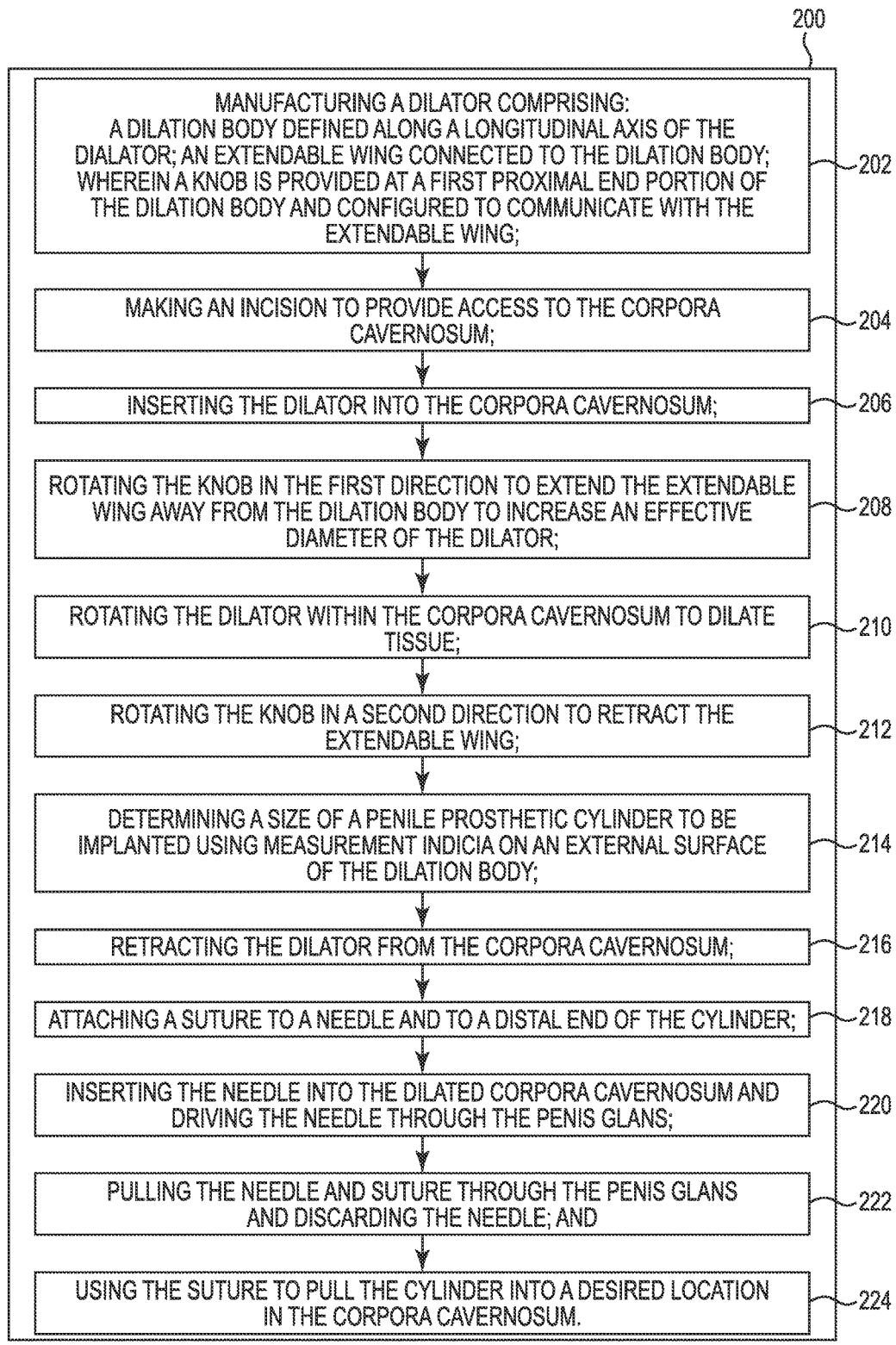
FIG. 11 is a box diagram indicating a method of implanting a penile prosthetic in a corpora cavernosum of a penis.

In a third aspect, the present disclosure relates to a method 200 of implanting a penile prosthetic in the corpora cavernosum of a penis. FIG. 11 is a box diagram indicating the method 200. At 202, the method includes manufacturing a dilator comprising: a dilation body defined along a longitudinal axis of the dilator and an extendable wing connected to the dilation body, wherein a knob is provided at a first proximal end portion of the dilation body and configured to communicate with the extendable wing. In embodiments, the dilator is a dilator according to the embodiments of the first aspect of the present disclosure. At 204, the method includes making an incision to provide access to the corpora cavernosum. Suitable examples of incisions are provided above. At 206, the method includes inserting the dilator into the corpora cavernosum. At 208, the method includes rotating the knob in a first direction to extend the extendable wing away from the dilation body to increase an effective diameter of the dilator. At 210, the method includes rotating the dilator within the corpora cavernosum to dilate tissue. At 212, the method includes rotating the knob in a second direction to retract the extendable wing. In embodiments, the steps 202, 204, 206, 208, 210, 212 correspond to the steps 102, 104, 106, 108, 110, 112 of the method 100 of dilating tissue of a corpora cavernosum of a penis according to the second aspect of the present disclosure.

At 214, the method includes determining the size of a penile prosthetic cylinder to be implanted using measurement indicia on an external surface of the dilation body. At 216, the method includes retracting the dilator from the corpora cavernosum. At 218, the method includes attaching a suture to a needle and to a distal end of the cylinder. At 220, the method includes inserting the needle into the dilated corpora cavernosum and driving the needle through the penis glans. At 222, the method includes pulling the suture through the penis glans and discarding the needle. At 224, the method includes using the suture to pull the cylinder into a desired location in the corpora cavernosum.

The present disclosure provides a dilator for dilating tissue of a corpora cavernosum of a penis that is adjustable to be set to different effective diameters. This eliminates the need for providing and preparing a set of dilators with individually different diameters. The present disclosure provides a versatile dilator that may additionally be used as a Furlow tool and as a cavernatome, thereby reducing or eliminating the need for individual Furlow and cavernatome tools. The present disclosure provides a method of dilating the tissue of the corpora cavernosum in which the surgeon can use the dilator according to the disclosure as a single dilator adjustable to different effective diameters. This reduces the number of tools necessary and saves time and money in preparation and execution of the procedure. Moreover, the present disclosure provides a method for implanting a penile prosthetic in a corpora cavernosum of a penis that requires use of fewer tools for the implantation to the benefit of both the surgeon and the patient.

Although specific embodiments have been illustrated and described, it will be appreciated by those of ordinary skill in the art that a variety of alternate and equivalent implementations may be substituted for the specific embodiments shown and described without departing from the scope of the present invention. This application is intended to cover any adaptations or variations of the kind of medical devices described above. Therefore, it is intended that this invention be limited only by the claims and their equivalents.

What is claimed is:

1. A dilator configured for dilating tissue of a corpora cavernosum of a penis, the dilator comprising:
   a dilation body having a proximal end, a distal end, and dilation body diameter;
   a wing having a width extending between a first edge that is connected to the dilation body by a hinge and a second edge that is not connected to the dilation body, the wing having a wing length extending between a proximal wing end and a distal wing end, the wing being curved between the first edge and the second edge and linear between the proximal wing end and the distal wing end, where the second edge of the wing includes a tissue cutting blade; and
   a knob connected to the proximal end of the dilation body;
   wherein the dilation body includes a transition recess formed over a part of a circumference of the dilation body, with the transition recess sized to receive the wing such that the dilator has a dilator diameter equal to the dilation body diameter when the wind is in a closed state;
   wherein the knob is attached to the wing such that rotation of the knob moves the wing to and open state with the second edge of the wing displaced away from the transition recess of the dilation body to increase an effective diameter of the dilator.

2. The dilator according to claim 1, wherein the knob is connected to the wing along a turn rod provided in the dilation body.

3. The dilator according to claim 1, wherein rotation of the know increases the effective diameter of the dilator up to two times.

4. The dilator according to claim 1, wherein the second edge of the wing defines a free edge of the wing.

5. The dilator according to claim 1, further comprising a lock button and a lock slot configured to maintain the wing in an extended position away from the dilation body.

6. The dilator according to claim 1, wherein the knob is configured to be turned in a clockwise direction for extension of the wing.

7. The dilator according to claim 1, wherein the dilation body tapers toward a central longitudinal axis of the dilator to a tapered diameter at the distal end of the dilation body that is smaller than the dilation body diameter.

8. The dilator according to claim 1, wherein the dilation body comprises an external surface provided with measurement indicia.

9. The dilator according to claim 1, wherein the wing extends from the proximal end, along a longitudinal axis of the dilator and along a portion, but less than an entirety, of the dilation body.

10. The dilator according to claim 1, wherein
    the dilation body includes a lumen extending through the dilation body from the proximal end to the distal end, and
    a needle slidably disposed within the lumen.

11. The dilator of claim 10, further comprising a plunger slidably disposed within the lumen.

12. The dilator of claim 11, wherein the plunger operates to slide the needle through the lumen and out of the distal end of the dilation body.

13. The dilator of claim 1, wherein a first curvature of an exterior surface of the wing is equal to a second curvature of an interior surface of the wing.

14. The dilator of claim 1, wherein when the dilation body is rotated, the tissue cutting blade is configured to remove tissue from the corpora cavernosum to form an opening in the corpora cavernosum, the opening having a dimension of the effective diameter of the dilator and so sized to receive a cylinder of an implantable penile prosthetic.

* * * * *